United States Patent [19]

Polaschegg et al.

[11] Patent Number: 4,835,477
[45] Date of Patent: May 30, 1989

[54] PROCESS FOR THE DETERMINATION OF THE HEMATOCRIT LEVEL OF WHOLE BLOOD AND APPARATUS FOR CARRYING OUT THE PROCESS

[75] Inventors: Hans-Dietrich Polaschegg; Detlef Westphal, both of Oberursel; Klaus Metzner, Friedrichsdorf, all of Fed. Rep. of Germany

[73] Assignee: Fresenius AG, Fed. Rep. of Germany

[21] Appl. No.: 86,495

[22] Filed: Aug. 14, 1987

[30] Foreign Application Priority Data

Aug. 16, 1986 [DE] Fed. Rep. of Germany ....... 3627814

[51] Int. Cl.$^4$ .................... G01N 27/06; G01N 27/26; A61B 5/05; G06G 7/60
[52] U.S. Cl. .................................... 324/439; 128/635; 204/406; 324/71.1; 324/441; 364/413.07; 436/70
[58] Field of Search .............. 324/425, 439, 441, 71.1, 324/71.4; 128/635; 204/400, 403, 406, 407; 436/70, 150; 364/413.07, 413.08, 413.09

[56] References Cited

U.S. PATENT DOCUMENTS

| | | | |
|---|---|---|---|
| 4,202,747 | 5/1980 | Buzza et al. | 204/400 X |
| 4,452,682 | 6/1984 | Takata et al. | 204/400 X |
| 4,484,135 | 11/1984 | Ishihara et al. | 324/71.1 |
| 4,547,735 | 10/1985 | Kiesewetter et al. | 324/450 |
| 4,686,479 | 8/1987 | Young et al. | 324/439 |

FOREIGN PATENT DOCUMENTS 3416956 12/1986 Fed. Rep. of Germany .
2308099 11/1976 France .

OTHER PUBLICATIONS

Biomed. Technik, vol. 27, (1982), P171-175; Kiesewetter et al.; Determination of Hematocrit by Measuring Impedance.

*Primary Examiner*—Gerard R. Strecker
*Attorney, Agent, or Firm*—Andrus, Sceales, Starke & Sawall

[57] ABSTRACT

There is described a method and apparatus for the determination of hematocrit levels in which both the conductivity of whole blood and the conductivity of blood plasma are determined together. While a conductivity cell (18) is being used for the determination of the conductivity of whole blood, the conductivity of plasma is calculated in a computer (30) with the aid of ion selective electrodes (14, 16) from the sodium or potassium concentrations.

14 Claims, 1 Drawing Sheet

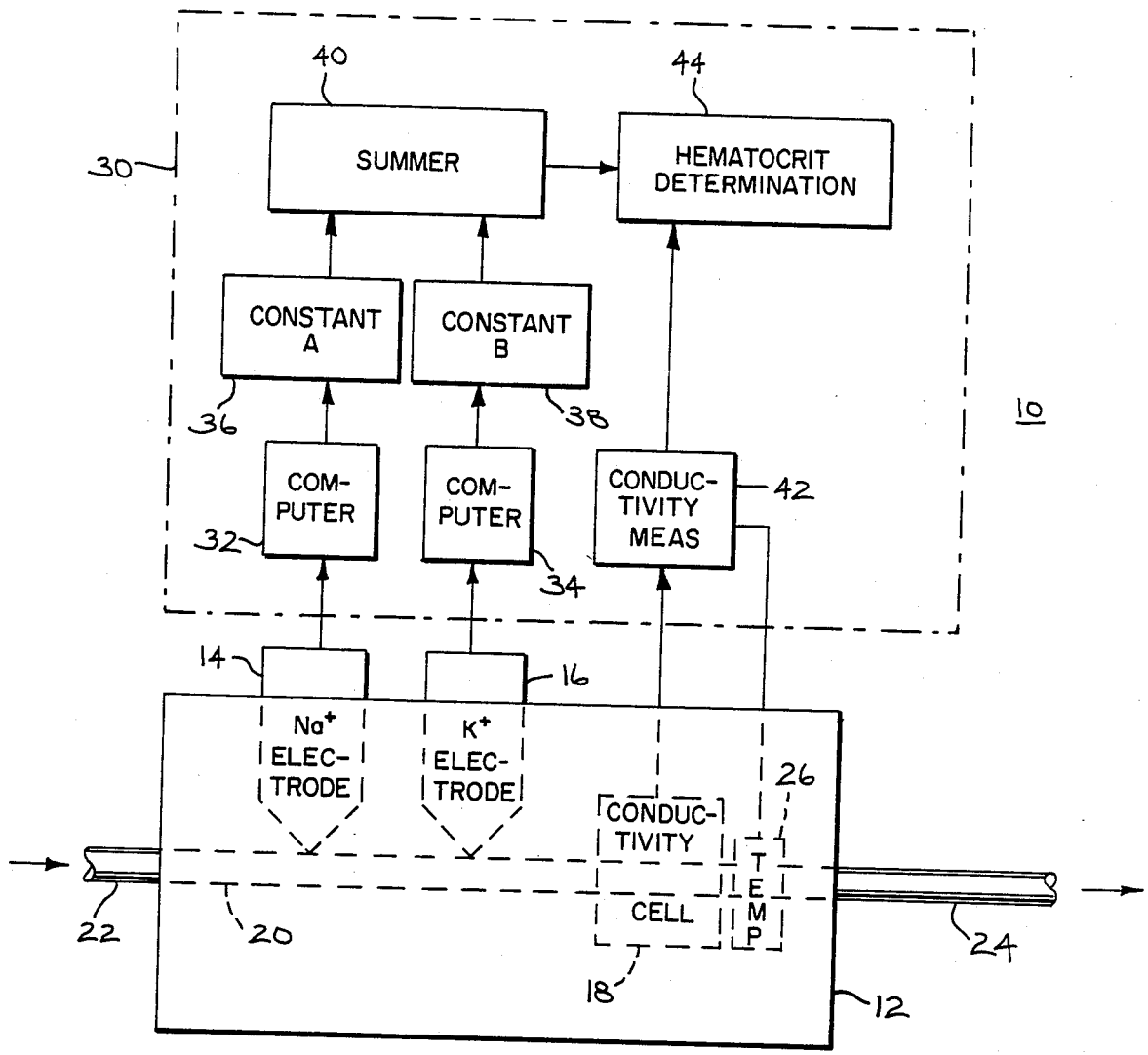

PROCESS FOR THE DETERMINATION OF THE HEMATOCRIT LEVEL OF WHOLE BLOOD AND APPARATUS FOR CARRYING OUT THE PROCESS

BACKGROUND OF THE INVENTION

The invention concerns a process for the determination of hematocrit in whole blood in which the conductivities of whole blood and blood plasma are determined and the hematocrit is determined from these conductivity values.

The invention also concerns an apparatus for the determination of hematocrit with means for the determination of the conductivity of whole blood, means for the determination of the conductivity of plasma and a unit for recording measured values.

Hematocrit is an important physiological parameter which is used in the assessment of the condition of a patient under medical care, particularly in the area of intensive medicine such as open heart surgery and dialysis treatment.

Conductivity measurement belongs to methods for the determination of hematocrit. Means for the determination of hematocrit levels of blood on the basis of conductivity measurement are described, for example, in U.S. Pat. specification No. 4,547,735 as well as the printed publications referred to in this specification and in Biomed. Techn., Volume 27 (1982), Pages 171 to 175. Here, a blood sample is measured in respect of its conductivity between two electrodes, in such a way that sedimentation effects in the blood sample do not falsity the measured value.

A measuring arrangement such as this requires a calibration curve with which the measured conductivity values can be compared.

Moreover, with the known means, the absolute conductivity is measured, not the specific conductivity, so that the constancy of the cell constant is a prerequisite. Incidentally, a temperature stabilization is definitely necessary with this process.

However, the use of such installed apparatus, in which a blood sample taken from a patient is placed between two electrodes becomes problematic if it is necessary to measure blood samples from the patient which have different electrolyte levels. The conductivity of the whole blood is then determined not only from the hematocrit, but also substantially from the conductivity of the medium conducting the current and of the blood liquid or plasma.

This, on the other hand, is strongly correlated to the electrolyte content. That is, it is dependent on the concentrations of the kinds of ions mainly determining the conductivity.

The plasma conductivity varies by about 15% with a variation in sodium ion concentration from 130 to 150 mmol/l with constant potassium of 4 mmol/l. From a calibration curve determined for 130 mmol/l sodium, a hematocrit of 30% would only be indicated as 22% to 23% hematocrit.

In cases of an electrolyte disturbance, calibration curves specific to patients would be necessary according to the hereinbefore described known process. The process fails completely if the electrolyte level changes during the treatment, as for example, in dialysis or the infusion of hyperosmolar or hypoosmolar liquids.

The determination of absolute hematocrit levels in extracorporeal dialysis in which the conductivity of whole blood and of plasma is determined has been described in U.S. Pat. specification No. 4,484,135. In the process the plasma is obtained from whole blood in an ultrafilter and afterwards the conductivity measurement is carried out.

From this it was able to be established that changes of hematocrit are correlated to changes in the blood volume provided that the volume of the erythrocytes remains substantially constant.

This known apparatus, however, has the disadvantage that it is very costly, partly because of the necessity that the plasma has to be obtained first by filtration. In addition, because of the known Gibbs-Donnan Effect, the hemofilter results in a change of the ion concentrations in dependence on the protein content. Such changes in conductivity can lead to small errors of a few percentage points in the determination of hematocrit.

Finally, a process for the determination of hematocrit is disclosed in French Patent Specification No. 2 308 099 in which a quantitatively recorded blood sample is added to a determined amount of electrolyte solution and the electrolyte of the blood sample to be quantitatively determined and the electrolyte of the electrolyte solution are identical. In this process the initial concentrations and the concentration of the electrolyte mixture are determined so that from this the resulting values of the hematocrit can be calculated.

SUMMARY OF THE INVENTION

The object underlying the invention is to provide a process in which both the conductivity of whole blood and the conductivity of plasma and therefore the absolute hematocrit level in whole blood can be determined.

This object is achieved in that the sodium ion concentration or chloride ion concentration existing in the blood is determined and from the resulting concentration value the plasma conductivity is determined.

The process according to the invention provides, first of all, the advantage that whole blood can be used directly both for the determination of the conductivity value of whole blood and for the determination of the conductivity of plasma.

At the same time, the conductivity of the plasma is formed, essentially, through the sodium ions or the chloride ions, whereby sodium, for example, provides up to about 97% of the conductivity and potassium, as well as the other cations, represent the remainder of about 3%. This different way of looking at things refers, in essence, to the conductivity changes dealt with here in the physiological area. If the conductivity contribution of the bicarbonate anions are regarded, in essence, as constant (changes of the bicarbonate concentration of ±4 mmol/l lead to a distortion of the hematocrit level of at most one percentage point) the change of the cations is correlated with a corresponding change of the chloride anions. A selective influence need not to be considered here in first approximation.

The use of ion selective electrodes is advantageous in this respect as the concentration, which is independent of the volume of the erythrocytes, is determined through these electrodes. The concentration resulting from this can be multiplied with the specific conductivity of the specific ions to be converted to the conductivity of the ions, from which the overall conductivity of the plasma can be calculated through corresponding extrapolation.

In a further embodiment, in addition to the sodium selective electrode, a potassium selective electrode can be used in order to determine more exactly, that is, at least 99%, the overall electrolyte conductivity in the plasma, whereby the indefinite electrolyte portion which, in essence, is due to magnesium and calcium ions, can be regarded as constant without significant error in respect of the overall conductivity.

These ion selective electrodes are advantageously provided for in a single apparatus together with a conductivity measuring device so that both the electrolyte contained in a blood sample and the conductivity can be determined at the same time without the separation of plasma from the whole blood by means of a hemofilter being necessary.

It is particularly advantageous to use a flow device which comprises a conduit in which the ion selective electrodes and the conductivity measuring cell are enclosed. The blood sample can be injected into such a conduit with the aid of a syringe or, alternatively, the end of the conduit can be connected with a blood conducting, extra-corporeal lead which is influenced by a pump whereby blood is continuously pumped through the flow measuring device. In this way, blood which is analysed in a flow analyser can be withdrawn continously from an extra-corporeal circulation which, for example, is set up during hemadialysis with the aid of a branching lead. In addition, a blood sample of this can alternatively be withdrawn through a permanent catheter which has been introduced into a blood vessel. This method can be used advantageously for the supervision of patients in an intensive care unit.

Further advantages, features and details are explained with reference to an embodiment shown in the drawing.

BRIEF DESCRIPTION OF THE DRAWING

The drawing is a block diagram of a flow arrangement with two ion selective electrodes and a conductivity cell according to the invention.

DETAILED DESCRIPTION

In the drawing, the apparatus for the determination of the hematocrit is designated 10. This apparatus 10 comprises a housing 12, in which a sodium ion selective electrode 14, a potassium ion selective electrode 16 and a conductivity cell 18 are accommodated, whereby the electrodes 14 and 16 are connected in well known manner with a reference electrode arrangement which is not shown. In addition, the housing 12 comprises a conduit 20 which is connected to an inlet connector 22 and an outlet connector 24.

The sodium ion selective electrode 14, the potassium ion selective electrode 16 and the conductivity cell 18 are connected in such a way that the blood to be transmitted through the conduit 20 comes into contact with them and consequently each can trigger a measuring signal.

Flow arrangements of that kind are known from published German Patent Specification No. 34 16 956 and reference is expressly directed to the disclosures of this specification. In this respect, further details of the ion selective electrodes (which, incidentally, are known) can be disregarded. Finally, conductivity measuring cells are also known and need not be explained in detail here.

Blood can be supplied to the conduit 20 with the aid of a supply fitting (not shown) and supported through this.

During measurement, the blood remains stationary in the conduit 20 and is afterwards driven out of the conduit 20 with a flushing fluid (air, sodium chloride solution or the like) in a cleaning operation.

The housing 12 can further comprise a thermostat control device (not shown) or a temperature measuring device 26 arranged on the conduit 20 in order to compensate temperature effects through stabilization or by computing means. The apparatus 10 can also therefore be in equilibrium with the surroundings; without this, thermostatic control would be necessary.

The sodium ion selective electrode 14, the potassium ion selective electrode 16 and the conductivity cell 18 are connected with a computer 30 which is shown in broken outline in the drawing. This computer 30 comprises the hereinafter described units with which the hematocrit level can be calculated from the signals emitted from the electrodes and the conductivity cell.

In the computing units 32 or 34, the sodium ion concentration $C_{Na}$ and the potassium ion concentration $C_K$ are first calculated respectively from the signals of the sodium ion selective electrode 14 and the potassium ion selective electrode 16. Moreover, the ion selective electrodes are calibrated according to a known process with standard solution in which the computing units 32 and 34 for the calculation of the ion concentrations compare the measured signals and therefore determine the actual ion concentration in the blood.

Empirical constants A and B are respectively assigned in the coordinating units 36 and 38 to the concentration values determined in the computing units 32 and 34 so that the product $A \times C_{Na}$ results from this for the sodium ion concentrations and the product $B \times C_K$ results from this for the potassium ion concentrations. The empirical sizes A and B are previously determined by experiment and therefore represent coefficients. They contain, in essence, the conductivity constants of the sodium or potassium ions in the relevant concentration range.

The products determined in the coordination units 36 and 38 therefore represent the conductivity of respective sodium and potassium ions in the plasma, to which additionally is added a constant D which takes into account the remaining magnesium and calcium ions contained in the blood. Moreover, the values determined in the units 36 and 38 are added in a summer 40 together with the constant D to the plasma conductivity, as clearly shown in Equations (1) and (2).

$$LF_p = (A \times C_{Na}) + E \tag{1}$$

$$LF_p = (A \times C_{Na}) + (B \times C_K) + D \tag{2}$$

in which, therefore, $E = (B \times C_K) + D$ and $LF_P$ represents the conductivity of plasma.

The conductivity measuring cell 18 and, where appropriate, the temperature measuring device 26 are connected with a unit 42 for determining the conductivity of whole blood whereby the determined value can if necessary be temperature compensated. This unit 42 calculates this conductivity value from the inputted signals and transmits the determined value to a unit 44 in which, from the following Equation (3)

$$Hk_t = K \times \left(1 - \frac{LF_{VB}}{LF_p}\right) = K \times N \tag{3}$$

the hematocrit level Hkt is determined, in which $LF_{VB}$ represents the conductivity of whole blood and the constant K is an empirical coefficient. Usually, all the hereinbefore mentioned constants K, A, B, D or E are standardized from a correlation measurement with known plasma conductivity values which result, for example, from the hemotocrit measurement in a centrifuge.

This unit 44 is furthermore fed with the conductivity determined in the summer 40 and determines the hematocrit according to the hereinbefore mentioned equation.

A conventional indicator (not shown) or a device for the storage of the determined values is connected to this unit.

It has been shown that the hematocrit value determined with this apparatus corresponds with the hematocrit value measured by centrifugal action. With ion selective electrodes, it is possible to determine the activity of ions and, by means of simple conversion, the concentration of ions in the aqueous phase of the blood. The conductivity of plasma can therefore be calculated from the ion concentrations in the whole blood determined with the aid of ion selective electrodes. With the aid of these determined plasma and whole blood conductivity values, the hematocrit value can be calculated—as hereinbefore explained.

As already hereinbefore mentioned, anion selective electrodes, for example, a chloride and (if appropriate) a biocarbonate selective electrode, can also be used instead of cation selective electrodes.

The hereinbefore mentioned relationship for hematocrit can only be adapted for a relatively narrow hematocrit range. It is advantageous to determine the hematocrit magnitude Hkt in a quadratic or cubic approximation in order to take account of the known non-linearity in the hematocrit-conductivity relationship. The hematocrit is thereby determined in the whole range of about 15% to 65%.

Moreover, the unit 36 or the summer 40 is provided with corresponding constants which, in combination with the ion concentrations, lead to the plasma conductivity values.

The chloride content of blood can be determined with a chloride ion selective electrode in the same way as the sodium concentration from which, in accordance with Equation (4).

$$LF_p = (F \times C_{Cl}) + G \qquad (4)$$

the hematocrit is calculated, in which the constants F and G on the other hand, like the hereinbefore constants K, etc., are empirical constants which are determined by comparison with known plasma conductivity values or hematocrit values.

Similarly, the constant K can be determined from blood samples with known hematocrit values, as hereinbefore mentioned.

It has now become apparent that usable hematocrit values, in which the whole blood conductivity is measured in $mS/cm^2$ and the concentrations are measured in mmol/l, are obtained with the following values.

The constant K lies in range of 72 to 88, preferably about 80, the constant A in a range of about 0.058 to 0.082, preferably about 0.07, the constant B at about $1.2 \times A$ and the constant D in a range of 0 to 2, preferably about 1. The hematocrit values determined with these values accord with the usual methods for the determination of hematocrit which themselves give different values, within about 2 to 3 hematocrit degrees, in which these constant are usable, particularly advantageously in a hematocrit range of about 18 to 48.

Besides this linear approximation a quadratic approximation is advantageously carried out according to the following Equation (5):

$$Hkt = (P \times N^2) + (Q \times N) \qquad (5)$$

in which the values P and Q were determined empirically from the hereinbefore mentioned method of calculation and N indicates the bracketed expression given in Equation (3). In this case, the constant P lies between about 37 and 57, preferably at about 47, and the constant Q between 44 and 60, preferably at about 52.

With the quadratic approximation, the Hkt measuring range can be widened to more than 60 and less than 15, whereby the existing deviations with the linear approximation can be maintained.

We claim:

1. A process for the determination of the hematocrit level of whole blood including the steps of:
   measuring the conductivity of the whole blood
   measuring the concentration of sodium ions or chloride ions in the whole blood
   determining the conductivity of blood plasma from the concentration of sodium ions or chloride ions in the whole blood, and
   determining the hematocrit level from the conductivity of the whole blood and the conductivity of blood plasma.

2. A process according to claim 1 in which the concentration of sodium ions in the whole blood is measured, the concentration of potassium ions in the whole blood is measured, and the conductivity of blood plasma is determined from the concentrations of sodium and potassium ions in the whole blood.

3. A process according to claim 2 in which the conductivity of blood plasma is calculated according to the linear equation $$LF_p = (A \times C_{Na}) + (B \times C_K) + D$$

in which $LF_P$ represents the conductivity of blood plasma, $C_{Na}$ represents the concentration of sodium ions in the whole blood, $C_K$ represents the concentration of potassium ions in the whole blood, and A, B and D are correlation constants which are determined from a known value of plasma conductivity.

4. A process according to claim 3 in which the constant K amounts to about 72 to 88, the constant A amounts to about 0.058 to 0.082, the constant B amounts to about $1.2 \times A$ and the constant D amounts to 0 to 2.

5. A process according to claim 4 in which the constant K is about 80, the constant A is about 0.07 and the constant D is about 1.

6. A process according to claim 2 in which use is made of a quadratic approximation corresponding to the equation $$Hkt = (P \times N^2) + (Q \times N)$$

in which Hkt represents the hematocrit level, P lies between 37 and 57, Q lies between 44 and 60, $N = 1 - (LF_{VB}/LF_P)$, $LF_{VB}$ represents the conductivity of whole blood, $LF_P$ represents the conductivity of blood plasma and equals $(A \times C_{Na}) + (B \times C_K) + D$ where $C_{Na}$ represents the concentration of sodium ions in the whole blood, $C_K$ represents the concentration of potassium ions in the whole blood, and A, B and D are correlation constants which are determined from a known value of plasma conductivity.

7. A process according to claim 6 to which P amounts to about 47 and Q amounts to about 52.

8. A process according to claim 1 in which the determination of ion concentrations is carried out with ion selective electrodes.

9. Apparatus for the determination of the hematocrit level of whole blood comprising:
   a device for measuring the conductivity of the whole blood,
   a device for determining the conductivity of blood plasma incorporating a sodium ion selective electrode for measuring the concentration of sodium ions in the whole blood or a chloride ion selective electrode for measuring the concentration of chloride ions in the whole blood and computing means (32 to 40) for the determination of the conductivity of blood plasma in response to a signal from the sodium ion selective electrode or the chloride ion selective electrode, and
   a determining unit (44) for receiving values from the device for measuring the conductivity of the whole blood and from the computing means (32 to 40) and for determining the hematocrit level from the conductivity of the whole blood and the conductivity of blood plasma.

10. Apparatus according to claim 9 in which the device for measuring the conductivity of the whole blood comprises a conductivity cell (18) and a calculating unit (42) for determining the conductivity of the whole blood from a signal obtained from the conductivity cell (18).

11. Apparatus according to claim 10 comprising a computer (30) incorporating the computing means (32 to 40), the calculating unit (42) and the determining unit (44) and in which the computing means (32 to 40) includes a summer (40) and both the summer (40) and the calculating unit (42) are connected to the determining unit (44) to supply signals respectively representative of the conductivity of blood plasma and the conductivity of the whole blood.

12. Apparatus according to claim 9 in which the device for determining the conductivity of blood plasma incorporates sodium ion selective and potassium ion selective electrodes, both of which are operable to supply signals to the computing means (32 to 40).

13. Apparatus according to claim 12 in which the computing means (32 to 40) comprises computing units (32 and 34) respectively for the determination of the sodium ion and potassium ion concentrations from signals from the sodium ion selective electrode (14) and the potassium ion selective electrode (16), coordinating units (36 and 38) with which the concentration values determined respectively in the computing units (32 and 34) are respectively multiplied with constants (A and B), and a summer (40) with which the values determined respectively in the coordinating units (36 and 38) are added together with a further constant (D).

14. Apparatus according to claim 12 in which the device for measuring the conductivity of the whole blood comprises a conductivity cell (18) and a conduit (20) for conveying the whole blood and a housing (12) which surrounds the ion selective electrodes (14 and 16), the conductivity cell (18) and the conduit (20).

* * * * *